United States Patent [19]

Ellis et al.

[11] Patent Number: 4,474,556
[45] Date of Patent: Oct. 2, 1984

[54] DENTAL IMPLANT

[75] Inventors: Willard H. Ellis, Round Rock; Jack C. Bokros, Austin; Axel D. Haubold, Liberty Hill, all of Tex.; Michael Jarcho, El Cajon, Calif.

[73] Assignee: Carbomedics, Inc., Austin, Tex.

[21] Appl. No.: 434,111

[22] Filed: Oct. 13, 1982

[51] Int. Cl.³ .............................................. A61C 8/00
[52] U.S. Cl. .................................................. 433/173
[58] Field of Search ....................... 433/173, 174, 175

[56] References Cited

U.S. PATENT DOCUMENTS 3,952,414  4/1976  Shovers et al. ...................... 32/10 A
4,178,686 12/1979  Riess et al. ............................ 433/173
4,195,409  4/1980  Child .................................... 433/175

FOREIGN PATENT DOCUMENTS 2600639  7/1976  Fed. Rep. of Germany ...... 433/174

Primary Examiner—Robert Peshock
Attorney, Agent, or Firm—Fitch, Even, Tabin & Flannery

[57] ABSTRACT

In a dental prosthesis having a post stem, a neck and a head, the stem has a terminal segment at the end opposite the head and an intermediate segment with an uneven surface between the terminal portion and the head. The radial extremities of the uneven surface extend precisely to the contour of a right circular cone tapering in the terminal direction, and the radial extremities of the outer surface of terminal portion extend radially outward beyond the contour of this cone. A socket is drilled into the alveolar bone using a drill bit having the same conical taper that the extremities of the uneven surface follow. The prosthesis is inserted into the socket with some pressure so that the terminal portion deforms the alveolar bone only at the deep end of the socket, locking the prosthesis into the socket and bringing the extremities of the uneven surface into firm surface contact with the wall of the socket.

9 Claims, 6 Drawing Figures

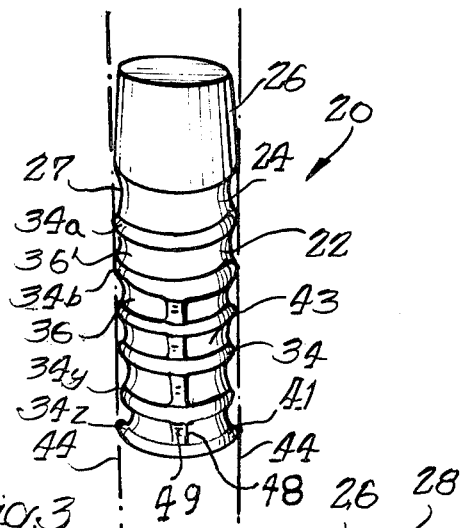
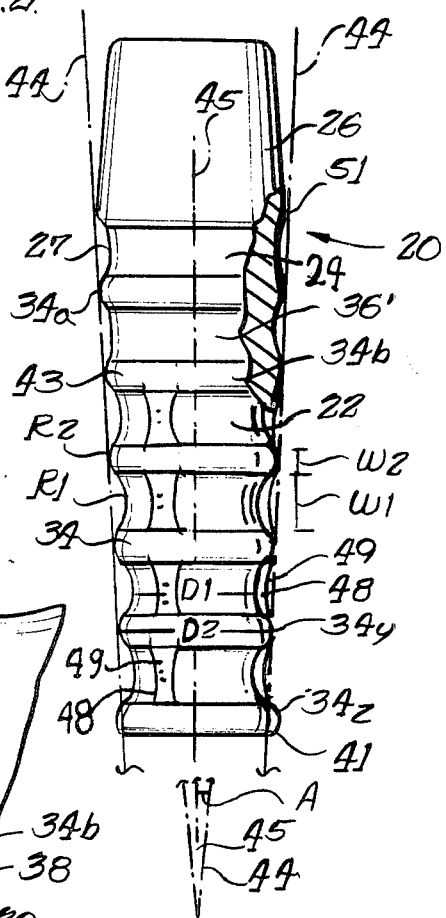
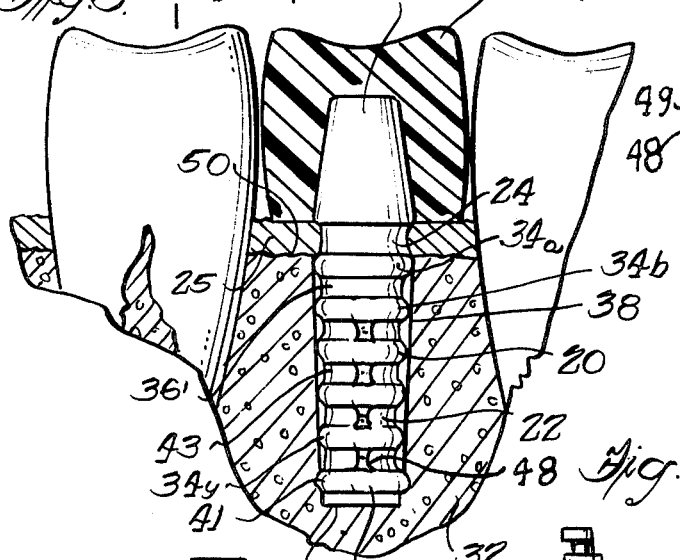
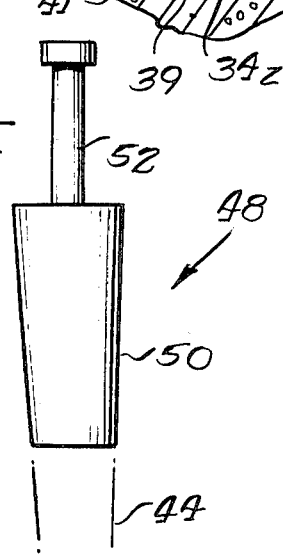
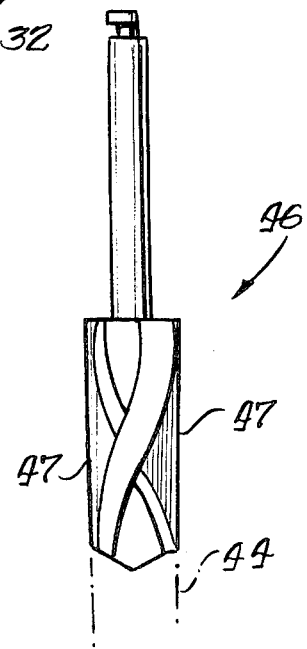
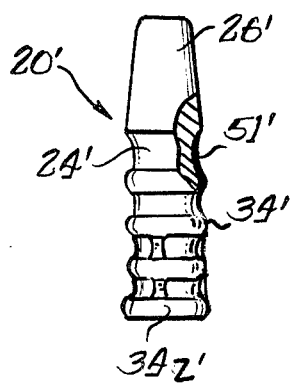

DENTAL IMPLANT

This invention relates to dental implants and more particularly to post stem dental implants for supporting artificial teeth.

BACKGROUND OF THE INVENTION

One type of dental implant has a post stem integrally attached through a short neck to a head for receiving a dental appliance, such as an artificial tooth. The post is inserted into a relatively deep socket or osteotomy formed in the alveolar bone so that the neck extends through the gingiva while the head protrudes above the surface of the gums. Typically, post stems have uneven outer surfaces for fixation within the alveolar bone through tissue ingrowth. An example of a dental implant having a post stem with an undulating surface is found in U.S. Pat. No. 4,195,409.

As a means of providing immediate immobilization of a dental implant within the alveolar bone, it is common practice to slightly undersize the socket and to force the stem thereinto. Unfortunately, the success rate of post stem dental implants has been less than would be desirable. The porous alveolar bone is particularly subject to deterioration, and it is believed that bone damage incurred by forcing an oversized stem into a narrow socket may accelerate bone deterioration. Hence, while forcing an oversize stem into a narrow socket may provide immediate immobilization, the fixation through tissue ingrowth, necessary for long-term stability, may not occur. Subsequent bone deterioration may actually result in loosening of the implant, and if this occurs, the implant may have to be removed.

Another cause of failure of post stem implants is the imprecision of the drilling operations which form the socket. Frequently, post stems are tapered for insertion into tapered sockets. Such sockets are commonly formed by a succession of drillings with several drill bits of different diameters. This process is slow and may result in burning of the bone tissue and other trauma. Frequently, due to imprecise drilling, the result of the successive drillings is not the desired undersized socket, but an oversized socket in which the implant fits loosely. An implant which is not immediately immobilized usually shifts when subjected to the stresses of mastication causing failure of the implant.

The need continues for dental prostheses which may be implanted with minimal disruption to the alveolar bone into which they are inserted and which have no mobility in the socket immediately after implantation.

SUMMARY OF THE INVENTION

A dental implant and method of insertion provide for immediate locking and immobilization of the implant into a prepared socket. The implant has a head, a neck and a stem, including an intermediate segment having an uneven outer surface with radial extremities that lie along the contour of a right circular cone and a terminal segment having an outer surface with radial extremities that extend beyond the contour of the right circular cone. A socket is drilled into the alveolar bone with a drill bit matched in taper to the intermediate segment, that is, the bit has edges which lie along the right circular cone. The implant is pressed into the prepared socket until its end segment deforms the alveolar bone at the deep end of the socket locking the implant in place with the radial extremities of the intermediate segment in firm surface contact with the sidewall of the socket fully immobilizing the implant.

BRIEF DESCRIPTION OF THE DRAWINGS

FIG. 1 is a perspective view of a post type dental implant embodying various features of the invention;

FIG. 2 is an enlarged elevation view of the post stem of the implant of FIG. 1 rotated 30° with respect to FIG. 1;

FIG. 3 is an elevation view of the implant of FIG. 1 implanted in an osteotomy formed in the mandible;

FIG. 4 is an elevation view of a tapered drill bit for forming the osteotomy that receives the post of the implant;

FIG. 5 is a perspective view of a try-in device for use in implanting the dental implant of FIG. 1; and FIG. 6 is a perspective view of an alternative embodiment of the dental implant of FIG. 1.

DETAILED DESCRIPTION OF THE PREFERRED EMBODIMENTS

Illustrated in FIG. 1 is a dental implant 20 having a post stem 22 integrally attached through a short neck portion 24 to a head 26 for receiving a dental appliance 28 (FIG. 2). The implant is shown in the upright orientation and will be described herein according to its implantation in the mandible in this upright orientation, understanding that the implant is inverted if it is implanted in the maxillia. The precise configuration of the implant 20 varies according to the location of insertion within the mouth, and the embodiment of FIG. 1 is particularly designed for supporting an artificial molar 28.

The head 26 has a configuration adapted for receiving a standard dental appliance, and herein, the head is in the shape of a truncated cone tapering towards its upper end. Preferably the head is no greater than 7 mm high so that it will accept any dental appliance without in situ reduction of the head. The neck 24, which extends through the gingiva 25 when the implant 20 is surgically inserted, consists of a groove 27 between the head 26 and the post 22.

As a means to provide for fixation of the stem 22 within the alveolar bone 32 through tissue ingrowth, the post 22 has an undulating configuration from end to end providing a plurality of annular ridges 34 alternating with a plurality of annular grooves 36. At least four and up to twelve ridges 34 are provided depending, in part, on the length of the post 22. It is intended that after the implant 20 is inserted into an osteotomy or socket 38, tissue will grow into the grooves 36 preventing displacement of the stem 22 by interfering with the ridges 34.

In the illustrated embodiment (see FIG. 2), the surfaces of the ridges 34 and grooves 36 in an axial direction are curved, and the concave radius of curvature R1 of the grooves 36 is substantially greater than the convex radius of curvature R2 of the ridges 34 whereby the grooves have a width (W1) about twenty-five to about one hundred and fifty percent greater than the width (W2) of the ridges in the axial direction. Although, this represents the preferred embodiment, in certain instances the radii (R1, R2) and/or the widths (W1, W2) of the ridges and grooves will be similar. The diameter D1 of the post 22 at the depth of each groove 35 is between about 50 and about 80 percent of the diameter D2 of the stem at the peaks of next lower adjacent ridge 34.

The post 22 has a generally tapered configuration for insertion into a tapered socket 38 that narrows towards its deep end 39. The post has a terminal segment 41 opposite the head 26 and an intermediate segment 43 between the terminal segment and the neck 24. The ridges 34 in the intermediate segment 43, successively decrease in diameter towards the terminal end. To provide for contact of the ridges 34 with a uniformly tapered socket, the ridges (with the exception of the terminal end ridge 34z) have diameters such that they are mutually tangential to the contour of a right circular cone 44, (represented in dot-dash in FIG. 2) which can be drawn along the post tapering toward the terminal end. The side of this cone tapers towards its axis 45 at an angle A of between about 2.5° and about 10°.

In accordance with the present invention, the terminal segment 41 has an outer surface with radial extremities that extend radially outward beyond the contour of the right circular cone 44 along which the radial extremities of the surface of the intermediate segment 43 lie. Thereby, when the post 22 is pressed into a socket 38 in the alveolar bone that has the configuration of a truncated portion of the right circular cone 44, the terminal segment 41 deforms the alveolar bone at the deep end 39 of the socket, and the intermediate segment is in firm surface contact with the sidewall of the socket, whereby the implant 20 is locked into and fully immobilized in the socket.

The terminal segment 41 comprises the terminal ridge 34z which has a diameter greater than the diameter which would make the terminal ridge tangential to the right circular cone 44, and generally the diameter of the terminal ridge is between about 0.04 and about 0.12mm greater than the diameter that would make the terminal ridge tangential to the cone. The post 22 is adapted for insertion into a socket 38 formed with the configuration of a truncated portion of the right circular cone 44 to a depth which permits full insertion of the post stem. Only the terminal ridge 34z must be forced into such a socket 38, and when the stem 22 is forced into the socket so that the terminal ridge is positioned closely adjacent to the deep end 39 of the socket 38, the remaining ridges 34 are in firm surface contact with the sidewall of the socket but do not deform the bone. Damage to the alveolar bone 32 resulting from forcing the post into the alveolar bone, therefore, is limited to a region adjacent to the deep end 39 of the socket.

As a means to prevent rotation of the implanted dental implant 20 within the socket 38, it is preferred that at least a portion of the implant stem 22 have a non-circular cross section. Herein, the lower end of the stem is made non-circular in cross section by the inclusion of vertical rows of fins 48 which extend between adjacent ridges 34. In the preferred embodiment, three rows of fins 48 are provided spaced 120° from each other so that one of the rows of fins 48 is likely to be implanted generally perpendicular to the line of teeth as shown in FIG. 3, whereby this row of fins will approximate a vertical plate in either the buccal or the lingual direction upon implantation, increasing anti-rotational stabilization. The fins 48 also serve to increase the overall strength and stability of the implant 20. Although additional rows of fins could be provided, such additional fins would reduce the volume of recess provided by the grooves.

The illustrated fins 48, as best seen in FIG. 2, have slightly concave outer surfaces 49; however, the depth of these surfaces relative to the cone 44 is substantially less than the depths of the corresponding grooves 36, i.e., typically less than about one-third of the depth of the grooves, whereby sufficient growth of tissue occurs inward of the outer fin surfaces 49 to prevent implant rotation.

Preferably, no fins are provided along the first groove 36' below the neck 24 so that uppermost ridge 34b to which fins 48 are associated will be implanted at least about 2 mm. below the upper surface 50 of the alveolar bone 32. Even if significant recision of bone and gingiva takes place over time, the patient will still be able to clean around the smooth groove 36' above the rows of fins 48.

The implant 20 is formed as a unitary structure from a strong biocompatible material, such as certain metals or ceramics or fine grained, high density graphites. Suitable metals include titanium, tantalum and chromium-cobalt alloys, such as those sold under the trademark Vitallium. A suitable graphite material is sold under the trademark Poco Graphite. A suitable ceramic material is aluminum oxide. Typically, ceramic implants are used for the more cosmetically important implants, such as those used to support artificial incisors.

To render the implant 20 fully biocompatible, it is preferred that an isotropic carbon coating 51 (FIG.2) is applied to at least those surfaces of the implant which contact body tissues. The carbon coating for the graphite structure 51 may be pyrolytically-deposited carbon, such as that sold under the trademark Pyrolite, the carbon coating for the metal and ceramic structures may be vapor-deposited carbon, such as that sold under the trademark Biolite. These carbon coatings are not recognized as foreign by the body and do not provoke rejective reactions. The layer of carbon 51 is thick enough to be impervious to liquids, but not so thick that it is likely to crack, and the carbon coating is typically, between about 0.1 and about 1.0 micron thick for the Biolite coating and about 0.5 mm thick for the Pyrolite coating. The Bacon Anistropy Factor is about 1.3 or lower, and the density is at least 1.5 g/cc. In addition to rendering the implants biocompatible, such a carbon coating 51 may have a porous surface whereby there is some ingrowth of tissue fibrils into the carbon surface.

For implants 20 which support artificial molars, it is generally most convenient to provide a uniform carbon coating 51 on the entire implant 20 including the head 26. Where a ceramic implant is provided for supporting a more visible artificial tooth, in the case of the vapor deposited coatings it is preferred that the carbon coating not be applied to the head 26 so that the coating does not produce a "shadow" in the artificial tooth.

Carbon coating 51 applied to the post 22 is unpolished so that the applied porous coating will promote the ingrowth of tissue fibrils. If the head 26 is coated, the surface of the carbon coating is unpolished to promote good bonding of an adhesive used to apply the dental appliance 28. On the other hand, the surface on the neck 24 is preferably polished so as to be non-irritating to the gingiva 25 through which the neck passes.

Rapid and accurate preparation of a tapered socket 38 is accomplished, in accordance with the invention, in a two drilling operations using first a pilot and then a tapered drill bit 46, such as that shown in FIG. 4. A drill bit 46 is provided for each size implant 20 having the exact taper of the implant 20; that is, the edges 47 of the drill bit lie along the contour of the right circular cone 44 to which the non-terminal ridges 34 of the implant 20 are mutually tangential. With the patient anesthesized and immobilized, the gingiva 25 is cut to expose the alveolar bone 32, and the socket 38 is drilled into the alveolar bone with the implant-matched bit 46 to a depth appropriate for the length of the post 22.

After debris is washed from the socket 38, the socket is checked for size with a metal try-in device 48 having an insertion portion 50 in the shape of a truncated cone (matched to the shape of the implant and drill bit) and a handle portion 52. If the try-in device 48 fits loosely, the socket 38 may have to be redrilled with a slightly larger bit 46 and a slightly larger implant 20 used. Most times, however, the final drilling provides a suitable socket 38, the limited drilling incurring far less bone burning and trauma than the severe drillings which are frequently used to provide non-cylindrical tapered osteotomies. The tapered drill bit 56 is adapted for relatively slow speed drilling, i.e., less than about 800 revolutions per minute, minimizing drill burn damage to bone tissue.

Because the socket 38 is in the shape of the cone 44 to which the non-terminal ridges 34 are tangential and because the terminal ridge 34z extends radially outward beyond this cone, the insert 20 does not slide freely to the full depth of the socket. However, the matched tapers of the post 22 and socket 38 allow the post to slide a substantial distance inward before the terminal ridge 34z encounters resistance to further insertion from the side of the socket.

Full insertion of the implant 20 is effected by forcing it the remaining distance into the socket 38. This may be accomplished with thumb pressure by the dental surgeon, the terminal ridge 34z being forced into the porous alveolar bone 32. Pressing the terminal ridge into the bone tissue locks the implant into the socket, the terminal ridge 34z slightly deforming the alveolar bone so that the implant might only be extracted with difficulty using pliers. At the same time, the remaining ridges 34 are brought into firm surface contact with the remainder of the socket 38, thereby fully immobilizing the implant 20. With the implant 20 in firm surface contact with the tapered socket 38 in several locations, i.e., along each ridge 34, the implant is not driven further into the alveolar bone by the stresses of mastication. Accordingly, very soon after implantation, the dental appliance 28 may be secured to the head 26 permitting the implant 20 to be used for mastication.

A typical molar implant 20 will now be described in greater detail. The implant 20 is formed of a graphite substrate having a uniform pyrolytic carbon coating 0.5 mm thick. The total height of the implant is 20 mm., the head 26 comprising about 4 mm. of this height and the neck 24 another 2 mm. The post 22 has six ridges 34, the peaks of each spaced about 2 mm. apart. The radius of curvature of the ridges 34 at their peaks is about 0.75 mm whereas the radius of curvature of the grooves 36 at their depths is about 0.5 mm. The longitudinal distance ($\frac{1}{2}W_1$ plus $\frac{1}{2}W_2$) from the peaks of the ridges 34 to the depths of the grooves 36 is about 1.25 mm. The non-terminal ridges 34 are tangential to the contour of a right circular cone 44 having a side that angles 10° relative to its axis. The uppermost ridge 34a has a peak diameter D2 of 5 mm. and the ridge 34y adjacent to the terminal ridge 34z has a peak diameter D2 of 3.8 mm. With this taper, the terminal ridge 34z would have a peak diameter of about 3.6 mm if it were to be tangential to the cone 44 to which the other ridges are tangential; however, it has a peak diameter D2 of 3.7 mm. or about 0.1 mm. greater than it would have if it were tangential to the right circular cone.

To insert the implant 20, the gingiva 25 around the region of tooth extraction is cut to expose the alveolar bone 32, and a socket 38 is drilled into the alveolar bone generally following the line of the root of the extracted molar. The socket 38 is formed to a depth of 14 mm. using a drill bit 46 precisely matched in taper to that of the implant 20. After examining the socket 38 with a try-in device 48, the implant 20 is inserted as far as it will go freely, i.e., to a depth of about 11 mm. Downward pressure on the head 26 forces the implant 2 mm. further into the socket 38 leaving about 1 mm of free space therebelow, the terminal ridge 34z being forced into the alveolar bone tissue and slightly deforming the alveolar bone at the deep end 39 of the socket. Full insertion of the implant 20 brings the remaining ridges 34 into firm surface contact with the side wall of the socket 38 fully and immediately immobilizing the implant 20.

The gingiva 25 is then sutured to fit closely around the neck 24. After a period of about 5 to 20 days, fixation is sufficient to permit the application of a dental appliance 28 in the form of an artificial crown or bridge to the head 26 of the implant, and at this time, the patient has full use of the implant for mastication.

Illustrated in FIG. 6 is an alternative embodiment of an implant 20', which may be used for replacement of an incisor. The post stem 22' is thinner and considerably shorter than the post stem of the molar implant 20, and the head 26' is also considerably thinner. The post 22' has only four ridges 34' (a terminal 34z' and three non-terminal ridges). The implant 20' is formed of aluminum oxide, and the neck 24' and post 22' are coated with a 0.5 micron layer of vapor-deposited carbon 51', while the head 26' is left uncoated.

While the invention has been described in terms of certain preferred embodiments, modifications obvious to one with ordinary skill in the art may be made without departing from the scope of the invention. For example, the ridges may be provided by cutting grooves into a smooth outer surface leaving ridges that have flat rather than rounded surfaces. The invention is intended to include implants having posts with uneven outer surfaces otherwise configured, providing that the radial extremities of the surface lie along the contour of a right circular cone except in a terminal portion where the radial extremities extend radially outward of the contour of the right circular cone.

Various features of the invention are set forth in the following claims.

What is claimed is:

1. A dental implant comprising a post for implantation into a preformed socket in the alveolar bone, a neck portion for extending through the gingiva and a head adapted to receive a dental appliance, said post having a terminal segment at the end opposite the head, and an intermediate segment between said neck and said terminal segment having an uneven outer surface, the raidal extremities of said uneven surface lying along the contour of a right circular cone tapering in the terminal direction, said terminal segment having an outer surface, the radial extremities of which extend between about 0.02 and about 0.06 mm. radially outward of the contour of the right circular cone, whereby said post may be inserted into the socket in the alveolar bone that is in the shape of a truncated portion of the right circular cone, said terminal segment of said post pressing into the bone and the radial extremities of said uneven intermediate surface in firm surface being contact with the sides of the socket.

2. A dental implant according to claim 1 having means to prevent rotation about an axis.

3. A dental implant according to claim 1 wherein said uneven surfaces comprise a plurality of annular ridges alternating with a plurality of grooves, each of said ridges in said intermediate segment extending to the contour of the right circular cone, said terminal segment having an annular ridge extending radially outward beyond the contour of the cone.

4. A dental implant according to claim 3 having at least four ridges including said terminal ridge.

5. A dental implant according to claim 1 wherein the sides of the right circular cone angle from its axis between about 2.5° and about 10°.

6. A dental implant comprising a post for implantation into a preformed socket in the alveolar bone, a neck portion for extending through the gingiva and a head adapted to receive a dental appliance, said post having a terminal segment at the end opposite the head and an intermediate segment between said neck and said terminal segment having an uneven outer surface, said uneven surface of said intermediate segment including a plurality of annular ridges alternating with a plurality of grooves, each of said ridges in said intermediate segment extending to the contour of a right circular cone that tapers in the terminal direction, said terminal segment having an annular ridge extending radially outward beyond the contour of the right circular cone, whereby said post may be inserted into the socket in the alveolar bone that is in the shape of a truncated portion of the right circular cone, said annular ridge of said terminal segment of said post pressing into the bone and said ridges of said intermediate segment being in firm surface contact with the sides of the socket, and said implant having fin means extending between said ridges for preventing rotation about an axis.

7. A method of implanting a dental prosthesis comprising
providing a dental prosthesis having a post for implantation into the alveolar bone, a neck for extending through the gingiva and a head adapted to receive a dental appliance, said post having a terminal segment at the end opposite said head and an intermediate segment between said neck and said terminal segment, said intermediate segment having an uneven outer surface, the radial extremities of said uneven surface lying along the contout of a right circular cone tapering in the terminal direction, said terminal segment having an outer surface, the radial extremities of which extend radially outward of the contour of the right circular cone,
surgically exposing the alveolar bone and preparing a socket in the alveolar bone in the shape of a truncated portion of the right circular cone to a depth sufficient to fully receive said post, and
inserting said prosthesis into said socket so that said terminal segment presses into the alveolar bone tissue, radially deforming the alveolar bone at the deep end of said socket and bringing the radial extremities of said uneven surface into firm surface contact with the wall of said socket.

8. A method according to claim 7 wherein said socket is drilled using a bit having edges tapered along the contour of the right circular cone.

9. A method according to claim 8 wherein said socket is formed with said bit at drill speeds of less than about 800 revolutions per minute.

* * * * *

UNITED STATES PATENT AND TRADEMARK OFFICE
CERTIFICATE OF CORRECTION

PATENT NO. : 4,474,556

DATED : October 2, 1984

INVENTOR(S) : Ellis et al.

It is certified that error appears in the above-identified patent and that said Letters Patent is hereby corrected as shown below:

Column 6, line 58    Correct the spelling of "radial".

Column 7, line 1     Change "in firm surface being" to --being in firm surface--.

Column 8, line 14    Correct the spelling of "contour".

Signed and Sealed this

Ninth Day of April 1985

[SEAL]

Attest:

DONALD J. QUIGG

Attesting Officer    Acting Commissioner of Patents and Trademarks